United States Patent [19]

Schulte-Elte et al.

[11] 4,453,011
[45] Jun. 5, 1984

[54] PROCESS FOR THE PREPARATION OF α,β- AND β,γ-UNSATURATED KETONES

[75] Inventors: Karl H. Schulte-Elte, Onex; Roger L. Snowden, Grand-Lancy; Bernard L. Muller, Geneva, all of Switzerland

[73] Assignee: Firmenich SA, Geneva, Switzerland

[21] Appl. No.: 405,989

[22] Filed: Aug. 6, 1982

[30] Foreign Application Priority Data

Aug. 14, 1981 [CH] Switzerland ..................... 5261/81

[51] Int. Cl.³ .............................................. C07C 45/51
[52] U.S. Cl. ..................................... 568/322; 568/403
[58] Field of Search ................ 568/322, 403, 361, 393

[56] References Cited

U.S. PATENT DOCUMENTS 3,887,625 6/1975 Schulte-Elte ....................... 568/393
3,976,700 8/1976 DeSimone .......................... 568/361

Primary Examiner—James H. Reamer
Attorney, Agent, or Firm—Pennie & Edmonds

[57] ABSTRACT

α,β- and β,γ-unsaturated ketones of formula

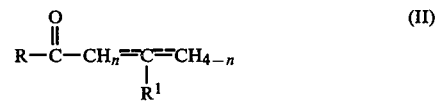

possessing a double bond in one of the positions indicated by the dashed lines and wherein R and $R^1$ have the meaning given above and index n stands for integer 1 or 2, are obtained by a process which consists in treating with a strong base in an inert organic solvent a diallyl carbinol of formula

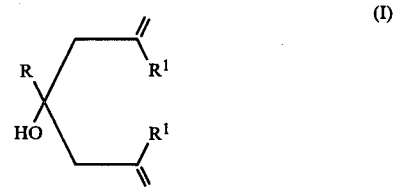

wherein symbol R represents a primary, secondary or tertiary alkyl radical, or a substituted or unsubstituted phenyl radical, and symbol $R^1$ represents a hydrogen atom or an alkyl radical.

4 Claims, No Drawings

PROCESS FOR THE PREPARATION OF α,β- AND β,γ-UNSATURATED KETONES

BRIEF SUMMARY OF THE INVENTION

The instant invention relates to a process for the preparation of α,β- and β,γ-unsaturated ketones which process consists in treating with a strong base in an inert organic solvent a diallyl carbinol of formula

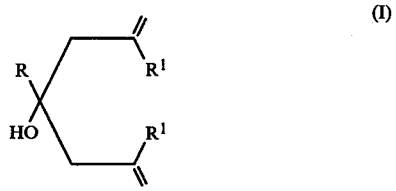

wherein sumbol R represents a primary, secondary or tertiary alkyl radical, or a substituted or unsubstituted phenyl radical, and symbol $R^1$ represents a hydrogen atom or an alkyl radical, to give a ketone of formula

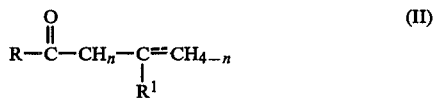

possessing a double bond in one of the positions indicated by the dashed lines and wherein R and $R^1$ have the meaning given above and index n stands for integer 1 or 2.

BACKGROUND OF THE INVENTION

Sofar, several synthetic methods have been reported in the patent literature and in various scientific publications, none of them however enables the direct conversion of esters into ketones in a way which is both economical and technically convenient. The present invention provides a solution to this problem.

The reaction which characterizes the process of the invention consists formally in an anionic splitting promoted by a strong base. To this end, mineral or organic bases such as alkali metal hydrides, alkoxides or hydroxides, preferably sodium or potassium derivatives, are used. Among the said bases one may cite especially sodium or potassium hydride, sodium or potassium tert-butoxide, sodium tert-amylate and sodium methoxide or ethoxide.

The choice among the bases cited above is determined by considerations of economy, safety and occupational health. As a consequence, alkoxides are preferred to hydrides, and among them potassium or sodium tert-butoxide is preferably used.

It could be established that the proportion of the base used must be equal to or higher than the required stoechiometric quantity. In reality, the best yields were achieved by the use of an excess of base.

The reaction times observed are relatively short. Thus at temperatures of about 70° to 80° C., the time of reaction is of the order of 2 to 3 hours when the base used is sodium hydride in a mixture of tetrahydrofuran and phosphorus hexamethyltriamide. Of course, temperature exerts a determining influence on reaction times. The process, which in itself is exothermic, can be carried out at a temperature near the room temperature. Values of between about 20° to 90° C. are preferred. At lower temperatures, the reaction times become too long, whereas at temperatures higher than the above given upper limit, we have observed the formation of unwanted by-products.

As described above, the reaction is effected in an inert organic solvent. Suitable solvents include ethers such as tetrahydrofuran or diisopropyl-ether, amides such as dimethylformamide or phosphorus hexamethyl-triamide. Mixtures of the above cited solvents can also be used. According to a preferred embodiment, potassium tert-butoxide is used as base and dimethylformamide or a mixture of dimethylformamide with tetrahydrofuran can be used as a solvent.

The invention is better illustrated by the following examples wherein the temperatures are indicated in degrees centigrade and the abbreviations have the meaning common in the art.

EXAMPLES

The addition of the appropriate diallyl alcohol to a mixture of potassium hydride (1.1 equivalents) in phosphorus hexamethyl-triamide (HMPT; 2 ml/mM of alcohol) at 20° and under a nitrogen atmosphere gives the corresponding alkoxide which is then heated directly in the same solvent at 80° for 2 hours.

The reaction mixture is then treated with a saturated aqueous solution of ammonium chloride and extracted with ether. The combined organic extracts were subjected to the usual treatments of washing, neutralization and evaporation of the volatile parts. The desired ketones were obtained by fractional distillation of the thus formed residue. The following table resumes the obtained results.

| | Starting materials | End-products | Yield (%) | Weight/ratio* |
|---|---|---|---|---|
| 1. | | | 75 | 3:1 |
| 2. | | | 79 | 2:1 |
| 3. | | | 79 | 4:1 |

| Starting materials | End-products | Yield (%) | Weight/ratio* |
|---|---|---|---|
| 4. 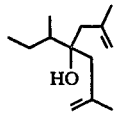 | 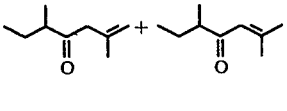 | 82 | 1:2 |
| 5. 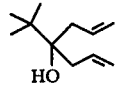 | 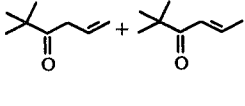 | 83 | 1:1 |
| 6. 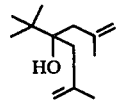 | 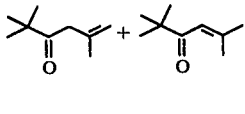 | 79 | 1:1 |
| 7. 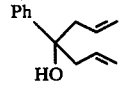 | 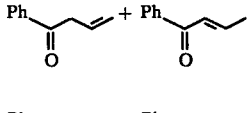 | 84 | 1:1 |
| 8. 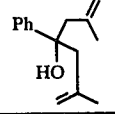 |  | 82 | 1:1 |

*relative to the presence of β,γ-isomer over α,β-isomer in the obtained mixture of ketones The analytical characteristics of the obtained compounds as well as those of the starting materials used for their preparation are indicated hereinafter.

1. 4-Butyl-1,6-heptadien-4-ol

B.p. 83°–85°/15 Torr;
IR: 3480, 3090, 1640, 1000, 920 and 880 cm$^{-1}$;
NMR: 0.90; 0.99; 1.32; 1.43 and 1.80 (9H); 1.55 (s, 1H); 2.23 (d, J=7 Hz, 4H); 4.97 and 5.20 (m, 4H); 5.83 (m, 2H) δppm;
MS: m/e: 127(10), 111(3), 85(100), 69(30), 57(94).

1-Octen-4-one and (E)-2-octen-4-one

B.p. 53°–56°/15 Torr and B.p. 81°/15 Torr;
IR: 1700, 1680, 1640, 1370, 1300, 1200, 980 and 922 cm$^{-1}$;
NMR: 0.92; 1.85–2.50; 3.13; 4.92–5.25; 5.92; 6.10 and 6.80 δppm;
MS: M$^+$=126; m/e: 111(13), 85(15), 84(18), 69(100), 57(28), 41(56).

2. 4-Butyl-2,6-dimethyl-1,6-heptadien-4-ol

B.p. 101°–102°/15 Torr;
IR: 3560, 3080, 1640, 1380, 1130, 1070, 892 and 780 cm$^{-1}$;
NMR: 0.90; 1.01; 1.37; 1.43 and 1.82 (9H); 1.62 (s, 1H); 1.84 (6H, m); 2.23 (4H, s); 4.77 and 4.93 (4H, m) δppm;
MS: m/e: 141(9), 85(100), 69(3), 57(92), 55(24).

2-Methyl-1-octen-4-one and 2-methyl-2-octen-4-one

B.p. 60°–64°/15 Torr;
IR: 3100, 1715, 1690, 1650, 1622, 1365, 1174, 1040 and 898 cm$^{-1}$;
NMR: 0.90; 1.75; 1.80–2.40; 3.09; 4.80; 4.90; 6.03 δppm;
MS: M$^+$=140(5); m/e: 125(1), 85(61), 83(45), 57(100), 41(39).

3. 4-(1-Methylpropyl)-1,6-heptadien-4-ol

B.p. 88°–89°/15 Torr;
IR: 3500, 3080, 1640, 1380, 1000, 915 and 760 cm$^{-1}$;
NMR: 0.85–2.0 (9H); 1.53 (s, 1H); 2.24 (d, J=7 Hz, 4H); 4.96 and 5.21 (m, 4H); 5.90 (m, 2H) δppm;
MS: m/e: 127(7), 111(4), 85(49), 69(39), 57(100).

5-Methyl-1-hepten-4-one and
(E)-5-methyl-2-hepten-4-one

B.p. 52°–55°/15 Torr;
IR: 3100, 1710, 1675, 1636, 1440, 1380, 1050, 996 and 920 cm$^{-1}$;
NMR: 0.70–2.80; 3.20; 5.00; 5.23; 5.62–6.30; 6.90 δppm;
MS: M$^+$=126(4); m/e: 111(2), 98(3), 85(14), 69(100), 57(41), 41(57).

4. 2,6-Dimethyl-4-(1-methylpropyl)-1,6-heptadien-4-ol

B.p. 102°–105°/12 Torr;
IR: 3560, 3080, 1640, 1380, 1070, 1000, 892 and 760 cm$^{-1}$;
NMR: 0.85–2.0 (9H); 1.68 (s, 1H); 1.83 (m, 6H); 2.22 (m, 4H); 4.75 and 4.92 (m, 4H) δppm;
MS: m/e: 141(7), 85(56), 57(100), 55(25), 41(17).

2,5-Dimethyl-1-hepten-4-one and
2,5-dimethyl-2-hepten-4-one

B.p. 62°–64°/15 Torr;
IR: 3090, 1710, 1690, 1624, 1460, 1380, 1040 and 898 cm$^{-1}$;
NMR: 0.72–2.80; 3.17; 4.80; 4.93 and 6.13 δppm;
MS; M$^+$=140(7); m/e: 85(32), 83(75), 57(100), 55(32), 41(32).

5. 4-(1,1-Dimethylethyl)-1,6-heptadien-4-ol

B.p. 80°–83°/15 Torr;

IR: 3090, 3050, 1640, 1400, 1370, 1000, 918 and 860 cm$^{-1}$;
NMR: 0.97 (s, 9H); 1.57 (s, 1H); 2.37 (d, J=7 Hz, 4H); 4.95 and 5.16 (m, 4H); 5.93 (m, 2H) δppm;
MS: m/e: 127(10), 111(5), 85(32), 69(71), 57(100).

2,2-Dimethyl-5-hexen-3-one and (E)-2,2-dimethyl-4-hexen-3-one

B.p. 48°–50°/15 Torr;
IR: 3100, 1700, 1635, 1480, 1400, 1370, 1320, 1300, 1120, 1060, 925 and 790 cm$^{-1}$;
NMR: 1.15 (s, 9H); 1.90 (d, J=6 Hz); 3.27 (d, J=7 Hz); 5.00; 5.22; 5.62–6.25; 6.80 δppm;
MS: M$^+$=126(3); m/e: 98(1), 85(15), 69(70), 57(100), 41(72).

6. 2,6-Dimethyl-4-(1,1-dimethylethyl)-1,6-heptadien-4-ol

B.p. 99°–101°/15 Torr;
IR: 3080, 3060, 1640, 1400, 1275, 1090, 995 and 892 cm$^{-1}$;
NMR: 0.98 (s, 9H); 1.77 (s, 1H); 1.87 (m, 6H); 2.30 (m, 4H); 4.79 and 4.88 (m, 4H); δppm;
MS: m/e: 141(5), 97(1), 85(23), 69(1), 57(100), 55(36), 41(20).

2,2,5-Trimethyl-5-hexen-3-one and 2,2,5-trimethyl-4-hexen-3-one

B.p. 60°–64°/15 Torr;
IR: 3090, 1710, 1686, 1652, 1622, 1480, 1370, 1320, 1070, 1008 and 893 cm$^{-1}$;
NMR: 1.17 (s, 9H); 1.77; 1.90; 2.10; 3.23; 4.75; 4.92; 6.30 δppm;
MS: M$^+$=140(2); m/e: 85(17), 83(36), 57(100), 55(22), 41(31).

7. 4-Phenyl-1,6-heptadien-4-ol

B.p. 127°–130°/15 Torr;
IR: 3500, 3080, 2990, 1640, 1500, 1448, 1000, 920 and 704 cm$^{-1}$;
NMR: 2.24 (s, 1H); 2.58 (m, 4H); 4.85–6.0 (6H); 7.35 (m, 5H) δppm;
MS: m/e: 147(18); 105(100), 91(1.3), 77(30), 51(6), 41(9).

1-Phenyl-3-buten-1-one and (E)-1-phenyl-2-buten-1-one

B.p. 105°–110°/15 Torr;
IR: 1680, 1640, 1600, 1580, 1450, 1338, 1210, 1180, 1004, 920, 760 and 697 cm$^{-1}$;
NMR: 2.00 (d, J=6 Hz); 3.72 (d, J=7 Hz); 5.10; 5.30; 5.80–6.50; 7.30–8.10 δppm;
MS: M$^+$=146(58); m/e: 131(27), 117(7), 105(100), 77(78), 69(57), 51(38).

8. 2,6-Dimethyl-4-phenyl-1,6-heptadien-4-ol

B.p. 73°–77°/0.01 Torr;
IR: 3550, 3080, 3040, 1640, 1498, 1443, 1380, 1070, 1030, 900, 730 and 700 cm$^{-1}$;
NMR: 1.40 (m, 6H); 2.53 (s, 1H); 2.60 (s, 4H); 4.68 and 4.86 (m, 4H) δppm;
MS: m/e: 161(8), 106(6), 105(100), 77(24), 55(3).

3-Methyl-1-phenyl-3-buten-1-one and 3-methyl-1-phenyl-2-buten-1-one

B.p. 115°–120°/15 Torr;
IR: 3080, 2995, 1700, 1675, 1620, 1600, 1580, 1450, 1380, 1250, 1210, 1180, 1010, 900, 760, 695 cm$^{-1}$;
NMR: 1.83; 2.03; 2.23; 3.70; 4.85; 4.98; 6.73; 7.25–8.10 δppm;
MS: M$^+$=160(6); m/e: 145(3), 105(100), 77(47), 5(16), 39(4).

According to the process of the invention, the obtained unsaturated ketones present respectively a α,β- and a β,δ-unsaturation. The mixtures of isomers can be separated by vapour phase chromatography or alternatively can be treated with an acidic isomerizing agent to give the α,β-isomer. Suitable isomerizing agents include the preferred p-toluenesulfonic acid and acidic diatomaceous earth.

1,6-Heptadien-4-ols used as starting materials in the process of the invention can be prepared with good yields by treating the appropriate carboxylic acid with allyl chloride or methallyl chloride under the conditions of a Grignard type reaction in tetrahydrofuran.

What we claim is:

1. A process for the preparation of α,β- and β,γ-unsaturated ketones of formula $$R-\overset{O}{\overset{\|}{C}}-CH_n-\underset{R^1}{\overset{}{C}}-CH_{4-n} \qquad (II)$$

having a double bond in one of the positions indicated by the dashed lines and wherein symbol R designates a primary, a secondary or a tertiary alkyl radical, or a substituted or unsubstituted phenyl radical, and wherein symbol R$^1$ represents a hydrogen atom or an alkyl radical and index n stands for integer 1 or 2, which comprises treating with at least a stoiciometric amount of a strong base in an inert organic solvent a diallyl carbinol of formula (I)

wherein symbols R and R$^1$ have the meaning indicated above.

2. A process according to claim 1 wherein the strong base is a hydride or an alkoxide.

3. A process according to claim 2 wherein the alkoxide is sodium or potassium tert-butoxide.

4. A process according to any of the preceding claims 1 to 3 wherein the reaction is carried out by means of potassium tert-butoxide in phosphorus hexamethyltriamide at a temperature of from about 50° to 90° C.

* * * * *